(12) United States Patent
Shirasaki et al.

(10) Patent No.: US 7,232,412 B2
(45) Date of Patent: Jun. 19, 2007

(54) BLOOD PRESSURE MEASURING APPARATUS

(75) Inventors: Osamu Shirasaki, Amagasaki (JP); Takeshi Kubo, Katsno (JP)

(73) Assignee: Omron Healthcare Co., Ltd., Kyoto (JP)

( * ) Notice: Subject to any disclaimer, the term of this patent is extended or adjusted under 35 U.S.C. 154(b) by 776 days.

(21) Appl. No.: 10/725,942

(22) Filed: Dec. 3, 2003

(65) Prior Publication Data

US 2004/0147848 A1   Jul. 29, 2004

(30) Foreign Application Priority Data

Dec. 3, 2002   (JP) .............................. 2002-351136

(51) Int. Cl.
*A61B 5/02*   (2006.01)
(52) U.S. Cl. .................. 600/490; 600/493; 600/494
(58) Field of Classification Search ................ 600/481, 600/483–485, 490–504
See application file for complete search history.

(56) References Cited

U.S. PATENT DOCUMENTS

| 5,316,006 | A |   | 5/1994 | Inage et al. |   |
|---|---|---|---|---|---|
| 5,715,828 | A | * | 2/1998 | Raines et al. | ................ 600/507 |
| 6,027,452 | A |   | 2/2000 | Flaherty et al. |   |
| 6,241,680 | B1 |   | 6/2001 | Miwa |   |
| 2003/0163051 | A1 | * | 8/2003 | Eckerle et al. | ............... 600/485 |

FOREIGN PATENT DOCUMENTS

| EP | 0560300 A1 | 3/1993 |
|---|---|---|
| EP | 0997102 A1 | 9/1999 |
| JP | 61-111405 | 7/1986 |
| JP | 2557976 Y2 | 12/1997 |

OTHER PUBLICATIONS

Chinese Office Action dated Jun. 24, 2005, directed to counterpart foreign application.
European Search Report dated Apr. 22, 2004.
* cited by examiner

*Primary Examiner*—Charles A. Marmor, II
*Assistant Examiner*—Navin Natnithithadha
(74) *Attorney, Agent, or Firm*—Morrison & Foerster LLP

(57) ABSTRACT

A blood pressure measuring apparatus oppresses blood vessels of a human body by an inflating unit through a cuff. When the blood vessels are oppressed through the cuff, a pulse wave superposed on a cuff pressure signal through a cuff pressure detector is detected by a pulse wave detector. The waveform of the detected pulse wave changes similarly to changes of pressure in the oppressed blood vessels in one heartbeat period. The information of the detected pulse wave waveform and the cuff pressure at this time are stored in a memory. A blood pressure calculator determines the scale of pulse wave waveform on the basis of the information stored in the memory, and matches the determined scale of pulse wave waveform with the scale of waveform showing pressure changes in the blood vessels, so that a plurality of timings of coincidence of cuff pressure and blood pressure are detected, and the systolic pressure and diastolic pressure are calculated by using these detected information and stored information of pulse wave waveforms. It is therefore possible to measure blood pressures in a short time.

15 Claims, 8 Drawing Sheets

BLOOD PRESSURE MEASURING APPARATUS

BACKGROUND OF THE INVENTION

1. Field of the Invention

The present invention relates to a blood pressure measuring apparatus and, more particularly, to a blood pressure measuring apparatus for oppressing arteries and measuring the blood pressures on the basis of the obtained results of the arterial volume changes.

2. Description of the Related Art

Methods for measuring blood pressures without giving stress include a method of detecting various pulsation signals (hereinafter, referred to as pulse waves) derived from volume changes of arteries to which pressure is applied from outside, in the process of varying the pressure gradually, and calculating and determining the blood pressures on the basis of the detected values (the method being referred to as oscillometric method). In a representative method, air or fluid is injected into an oppression band (cuff) which is wound around the blood pressure measuring position, and the arteries in the measuring position are oppressed. Pulse waves are detected as pulsations of oppressing pressure, that is, the cuff pressure, and this method is mostly widely employed (hereinafter, referred to as cuff oscillometric method) (see, for example, Japanese Unexamined Patent Publication No. 5-31084 (1993), specification and drawings and Japanese Unexamined Patent Publication No. 6-133938 (1994), specification and drawings).

In the cuff oscillometric method, pulse waves are extracted from cuff pressure signals, and in other oscillometric method, for example, other pulse wave detector (for example, photoelectric sensor) is additionally installed. Alternatively, an oscillometric method may be realized by oppressing arteries by other oppressing function than the cuff. All these varieties are called the oscillometric method in the following description.

A method of detecting the blood pressure at a certain time is disclosed in Japanese Published Patent Publication No. 2000-512875, pages 30–31, FIG. 27, and FIG. 29A to FIG. 29C. In this method, by obtaining the arterial volume signal when the cuff pressure is equal to or less than the diastolic pressure and the arterial volume signal when the cuff pressure is somewhere between the diastolic pressure and systolic pressure, the two obtained arterial volume signals are compared by matching the start timing; therefore, the moment of coincidence of cuff pressure and arterial pressure is known.

In the oscillometric method, for example, when measuring while increasing the cuff pressure, as shown in FIG. 12, blood pressures (systolic pressure and diastolic pressure) are estimated from the envelopes showing amplitude change patterns of pulse waves changing in the process of gradual elevation of the cuff pressure until sufficiently higher than the maximum pressure (systolic pressure). Although not shown in the drawing, when measuring while decreasing the cuff pressure, the cuff pressure is once raised quickly sufficiently higher than the systolic pressure, and is gradually decreased until sufficiently lower than the minimum pressure (diastolic pressure), and in this process, similarly, the blood pressures are estimated from the envelopes of pulse waves. In such estimating method, a high pressure level and a long measuring time are required according to its principle. A high pressure level often causes pain in a patient with hypertension. Pain during measurement of blood pressure is not only unpleasant, but also causes to raise the blood pressure, thereby causing effects on accuracy of blood pressure measurement. In addition, if one measurement takes a long time, not only the efficiency is lowered, but also the pain lasts for a long time, and the accuracy is sacrificed. Further, sudden blood pressure fluctuations often occurring during measurement or measurement during exercise cannot be correctly detected.

SUMMARY OF THE INVENTION

It is hence a primary object of the invention to provide a blood pressure measuring apparatus capable of shortening the measuring time.

It is another object of the invention to provide a blood pressure measuring apparatus capable of measuring without applying high pressure.

In accordance with an aspect of the invention, a blood pressure measuring apparatus comprises: oppressing means for oppressing blood vessels of a human body; oppressing pressure detecting means for detecting the oppressing pressure value on the blood vessels by the oppressing means; similar waveform detecting means for detecting similar waveforms changing similarly to pressure changes in the blood vessels oppressed by the oppressing means in one heart beat period; and blood pressure calculating means for determining the scale of the similar waveforms detected by the similar waveform detecting means, and calculating the blood pressure by matching the determined scale of similar waveforms with the scale of waveforms showing pressure changes in the blood vessels.

The blood pressure calculating means includes level detecting means for detecting the level of the similar waveforms in one heartbeat period, and means for determining the scale of the similar waveforms on the basis of the similarity ratio indicated by the ratio of the difference of levels at two moments of maximum level and minimum level detected by the level detecting means and the difference of the oppressing pressure values detected by the oppressing pressure detecting means corresponding to the two moments, and matching the determined scale of similar waveforms with the scale of the waveforms showing pressure changes in the blood vessels.

Therefore, since the blood pressure can be calculated by using the scale of similar waveforms changing similarly to the pressure changes in the blood vessels detected in one heartbeat period, the blood pressure can be measured in a short time. That is, once determining the scale of similar waveforms, the similarity ratio of matching the determined scale of similar waveforms with the scale of waveforms showing changes of pressure in the blood vessels can be easily obtained by the ratio of the difference of levels at two moments and the difference of oppressing pressure values detected by the oppressing pressure detecting means corresponding to the two moments. The levels at the two moments are somewhere between the maximum level and minimum level, and hence it is possible to measure without oppressing to the maximum level, that is, the maximum blood pressure. Since it is possible to measure by detecting only the levels of the two moments and the oppressing pressure value, the measuring time can be shortened.

Preferably, the two moments correspond to the starting moments of closure of the blood vessels by the two different oppressing pressure values to the blood vessels by the oppressing means.

Therefore, the starting moment of closure corresponds to the moment when the oppressing pressure and the pressure in the blood vessels are equalized, and by using the oppressing pressure value when the closure is started, the blood pressure can be calculated precisely.

Preferably, the similar waveforms are waveforms of pulse waves derived from pulsation components of volume changes of the blood vessels caused by oppression by the oppressing means.

Therefore, waveforms of pulse waves can be as similar waveforms.

Preferably, the blood pressure calculating means includes systolic pressure calculating means for calculating the oppressing pressure value corresponding to the maximum level as the systolic pressure, on the basis of the difference between the maximum level detected by the level detecting means and one level of the levels at two moments detected by the level detecting means, the oppressing pressure value detected by the oppressing pressure detecting means corresponding to the moment of the one level, and the similarity ratio.

Therefore, the systolic pressure can be calculated by using the maximum level of similar waveforms, one level of the levels at two moments, the oppressing pressure value corresponding to the one level, and the similarity ratio, and hence the blood pressure can be measured without oppressing the blood vessel to a high pressure close to the systolic pressure.

Preferably, the blood pressure calculating means includes diastolic pressure calculating means for calculating the oppressing pressure value corresponding to the minimum level as the diastolic pressure, on the basis of the difference between the minimum level detected by the level detecting means and one level of the levels at two moments detected by the level detecting means, the oppressing pressure value detected by the oppressing pressure detecting means corresponding to the moment of the one level, and the similarity ratio.

Therefore, the diastolic pressure can be calculated by using the minimum level of similar waveforms, one level of the levels at two moments, the oppressing pressure value corresponding to the one level, and the similarity ratio.

According to another aspect of the invention, a blood pressure measuring apparatus comprises: oppressing means for oppressing blood vessels of a human body; similar waveform detecting means for detecting similar waveforms changing similarly to pressure changes in the blood vessels oppressed by the oppressing means in one heart beat period; and blood pressure calculating means for determining the scale of the similar waveforms detected by the similar waveform detecting means, and calculating the blood pressure by matching the determined scale of similar waveforms with the scale of waveforms showing pressure changes in the blood vessels.

The similar waveform detecting means includes pulse wave detecting means for detecting the waveform of pulse waves derived from pulsation components of volume changes of the blood pressure caused by oppression by the oppressing means as the similar waveforms, and the blood pressure calculating means includes: storing means for storing, in the one heartbeat period, the levels of waveforms of first, second and third pulse waves detected by the pulse wave detecting means by first oppressing pressure not closing the blood vessels by the oppressing means, and second oppressing pressure and third oppressing pressure for closing the blood vessels; level specifying means for specifying the second and third level corresponding to the starting moments of closure of the waveforms of the second and third pulse waves, of the waveform of the first pulse wave matched in time phase with the waveforms of the second and third pulse waves, in the contents stored in the storing means; and processing means for determining the scale of the similar waveforms on the basis of the difference of the second level and third level specified by the level specifying means, and the similarity ratio indicated by the ratio of the difference of the second oppressing pressure and third oppressing pressure, and matching the determined scale of the similar waves with the scale of the waveform indicating the pressure changes in the blood vessels.

Therefore, since the blood pressure can be calculated by using the scale of similar waveforms changing similarly to the pressure changes in the blood vessels detected in one heartbeat period, the blood pressure can be measured in a short time. That is, by detecting the first, second and third pulse waves by the pulse wave detecting means and storing the waveform levels of the first, second and third pulse waves in the storing means for one heartbeat period, the scale of similar waveforms is determined on the basis of the similarity ratio by the processing means, and the blood pressure can be measured by matching the detected scale of similar waveforms with the scale of the waveforms showing pressure changes in the blood vessels.

Preferably, the processing means divides a second change amount as change amount of waveform of the first pulse corresponding to the difference between the maximum level of the waveform of the first pulse stored in the storing means and the second level, by a first change amount as change amount of waveform of the first pulse wave corresponding to the difference of the second level and third level, multiplies the obtained amount by the difference of the second oppressing pressure and third oppressing pressure, adds the second oppressing pressure to the product, and calculates the result as the systolic pressure.

Preferably, the processing means divides a second change amount as change amount of waveform of the first pulse corresponding to the difference between the minimum level of the waveform of the first pulse stored in the storing means and the third level, by a first change amount as change amount of waveform of the first pulse wave corresponding to the difference of the second level and third level, multiplies the obtained amount by the difference of the second oppressing pressure and third oppressing pressure, subtracts the product from the third oppressing pressure, and calculates the result as the diastolic pressure.

Preferably, in the blood pressure measuring apparatus, the waveforms of the first, second and third pulse waves are matched in time phase on the basis of the moment corresponding to the maximum levels of the waveforms stored in the storing means.

Therefore, the time phase can be matched on the basis of the stored contents in the storing means.

Preferably, the blood pressure measuring apparatus further comprises electrocardiographic detecting means for detecting electrocardiographic signals from a person to be measured simultaneously with measurement of blood pressures, in which the waveforms of the first, second and third pulse waves are matched in time phase on the basis of the characteristic waveforms in the electrocardiographic signals detected by the electrocardiographic detecting means in the one heartbeat period.

Therefore, the waveforms can be matched in time phase precisely on the basis of the characteristic waveforms synchronized with the heartbeats of the electrocardiographic signals.

Preferably, the characteristic waveforms show the peak of R waves. Therefore, the time phase can be matched precisely on the basis of the peaks of R waves having small noise components.

Preferably, the blood pressure calculating means includes pulse pressure calculating means for calculating the pulse pressure. Therefore, both blood pressure and pulse pressure can be measured.

Preferably, the pulse pressure calculating means calculates the pulse pressure on the basis of the difference of the maximum level and minimum level and the similarity ratio.

Preferably, the blood pressure calculating means further includes closure start point detecting means for detecting the start moment of closure of the blood vessels, and the closure start point detecting means detects the moment of start of closure by selecting the candidate moment showing the maximum difference between the slope level corresponding to the candidate moments of the similar waveforms and the slope level corresponding to the immediately preceding candidate moment, among a plurality of candidate moments from terminal end moment of the one heartbeat period to the moment corresponding to the maximum level.

Therefore, the start point of closure can be detected by using the slope level of similar waveforms.

Preferably, the blood pressure measuring apparatus further comprises a first measuring unit including the similar wave detecting means and blood pressure calculating means, and a second measuring unit for measuring the blood pressure according to the oscillometric method while gradually changing the oppression to the blood vessels by the oppressing means, in which one of the first and second measuring units is selectively activated.

Therefore, by selectively activating the second measuring unit, blood pressure measurement conforming to the conventional oscillometric method is also realized.

DESCRIPTION OF THE PREFERRED EMBODIMENT

Hereinafter, a preferred embodiment of the present invention will be described in detail with reference to the accompanying drawings. In this embodiment, as the principle of oscillometric method, pulse waves (cuff pressure pulse waves) superposed on the cuff pressure signals are detected, but the pulse waves are not limited to the cuff pressure pulse waves, and the pulse waves may be detected according to the optical or electrical principle.

Configuration of Apparatus

Figure 1:
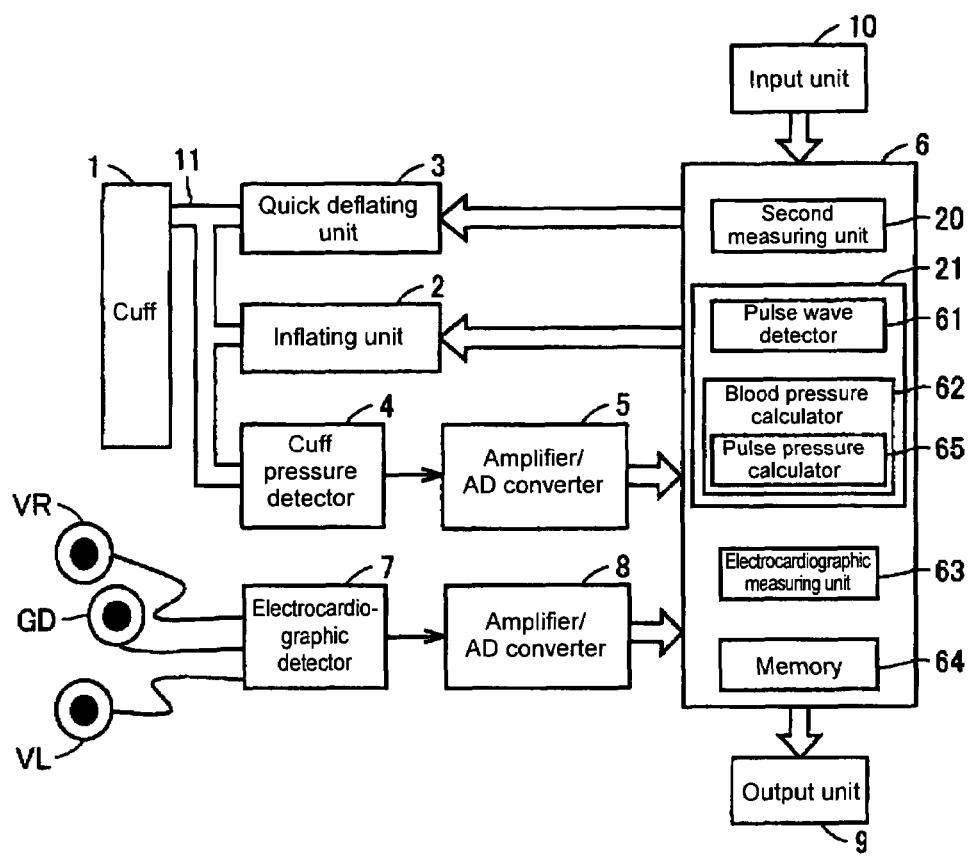
FIG. 1 is a functional configuration diagram of a blood pressure measuring apparatus according to an embodiment of the present invention.

Referring to FIG. 1, a blood pressure measuring apparatus according to the present invention comprises: a cuff 1 wound around an arm of a blood pressure measuring position; an inflating unit 2 including a pressurizing pump for applying cuff pressure to the cuff 1; a quick deflating unit 3 including a valve for quickly decreasing the cuff pressure of the cuff 1; a cuff pressure detector 4 including a sensor for detecting the cuff pressure; a microprocessor (hereinafter, referred to as MPU) 6 for centrally controlling and monitoring the blood pressure measuring apparatus itself; an amplifier/AD converter 5 for receiving an analog cuff pressure signal detected by the cuff pressure detector 4, amplifying, converting into a digital signal, and outputting to the MPU 6; an electrocardiographic detector 7 connecting left and right electrodes VL and VR and ground electrode GD; an amplifier/AD converter 8 for receiving an analog electrocardiographic signal detected by the electrocardiographic detector 7, amplifying, converting into a digital signal, and outputting to the MPU 6; an output unit 9 for outputting information about measured blood pressure and electrocardiographic waveform; and an input unit 10 for receiving instruction or information.

The quick deflating unit 3, the inflating unit 2 and the cuff pressure detector 4 are connected to the cuff 1 through an air system 11. The quick deflating unit 3 and the inflating unit 2 are controlled by the MPU 6. The MPU 6 has a blood pressure measuring function by a second measuring unit 20 and a first measuring unit 21, and has an electrocardiographic measuring unit 63 for measuring the electrocardiogram in parallel to blood pressure measurement, and a memory 64 for storing data necessary for various signal processings. The second measuring unit 20 has a function of measuring the blood pressure according to the conventional oscillometric method by gradually increasing or decreasing the oppressing pressure to the blood vessels by the inflating unit 4 between the vicinity of diastolic pressure and the vicinity of systolic pressure. The first measuring unit 21 includes: a pulse wave detector 61 for receiving a cuff pressure from the amplifier/AD converter 5 and detecting the pulse wave from the received cuff pressure signal; and a blood pressure calculator 62 for calculating the blood pressure by matching the amplitude changes of the detected pulse waves with the cuff pressure. The blood pressure calculator 62 has a pulse pressure calculator 65 for calculating the pulse pressure.

Figure 2:
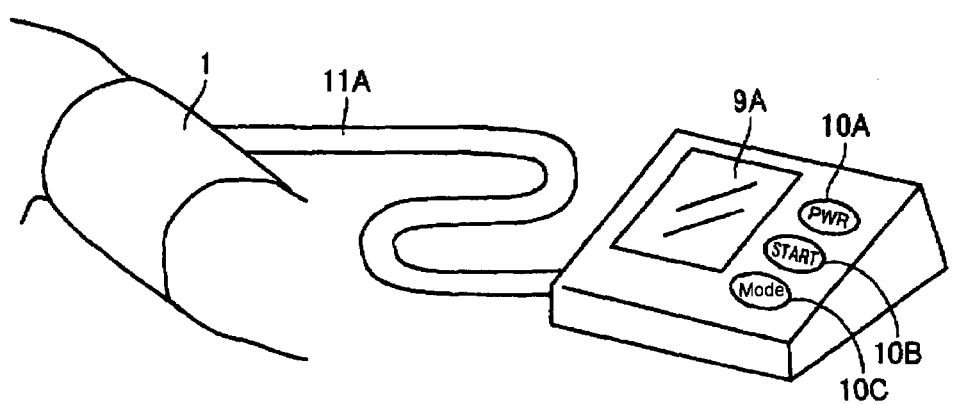
FIG. 2 is an appearance view of the blood pressure measuring apparatus according to the embodiment.

FIG. 2 shows an appearance of the blood pressure measuring apparatus shown in FIG. 1. In FIG. 2, the section for electrocardiographic detection is not shown. The blood pressure measuring apparatus in FIG. 2 comprises: a power switch 10A as the input unit 10; a start switch 10B manipulated for instructing start of measurement; a mode switch 10C manipulated for selecting the blood pressure measuring mode by one of the first and second measuring units 21 and 20; a display unit 9A as the output unit; and an air hose 11A as the air system 11. By manipulating the mode switch 10C, blood pressure measurement by one of the measuring units is activated.

Description of Blood Pressure Measuring Principle

Description will be given of the blood pressure measuring principle using estimation of blood pressure according to the embodiment. An artery applied with a pressure from outside by the cuff 1 changes in its volume depending on the magnitude relation between the external pressure, that is, the cuff pressure and the arterial pressure. Since the arterial pressure pulsates (changes) between the systolic pressure and diastolic pressure within one heartbeat period, the arterial volume changes accordingly. This volume change is detected as the cuff pressure change, which is known as pulse wave used in blood pressure calculation in the oscillometric method. The left sides in FIGS. 3A to 3C show an arterial pressure waveform 12 according to cuff pressure changes in one heartbeat period, respectively, and the right sides show an arterial volume waveform 13 showing volume changes due to arterial pressure waveform in one heartbeat period, that is, waveforms of pulse waves, respectively.

Figure 3A:
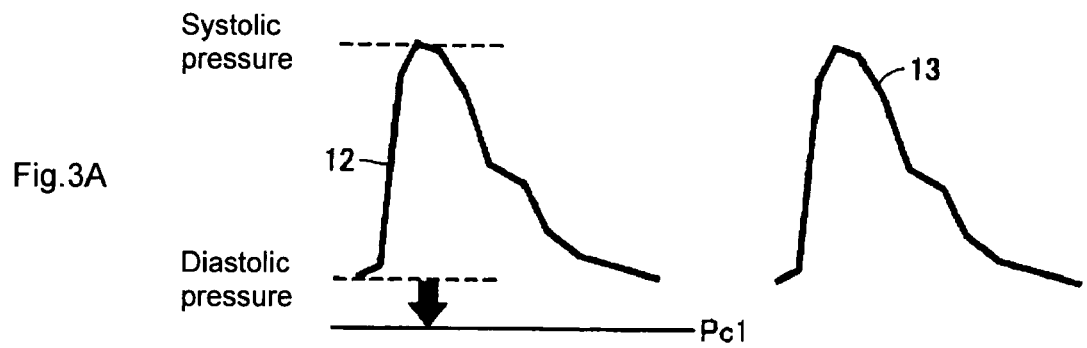
FIGS. 3A to 3C are descriptive diagrams showing the principle of blood pressure measurement using the blood pressure estimation according to the embodiment.

As shown in FIG. 3A, at a low cuff pressure Pc1 not reaching up to the systolic pressure, since the arterial volume waveform 13 and arterial pressure waveform 12 are almost similar to each other, the pulse waves detected as cuff pressure changes have also similar waveforms.

Figure 3B:
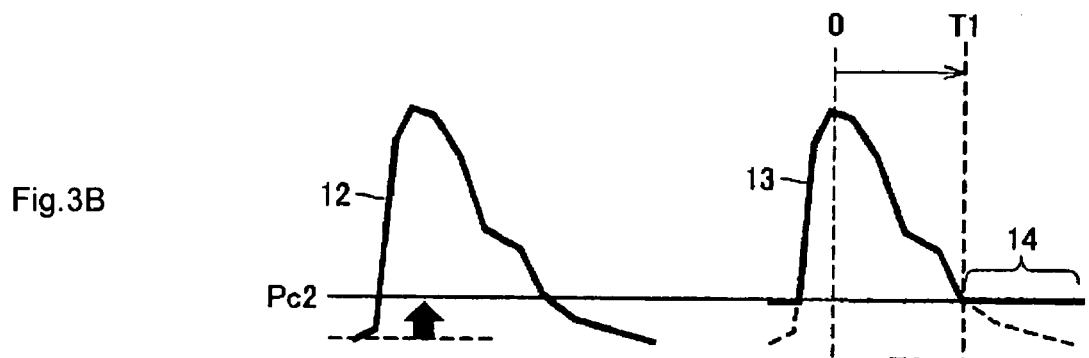
Figure 3C:
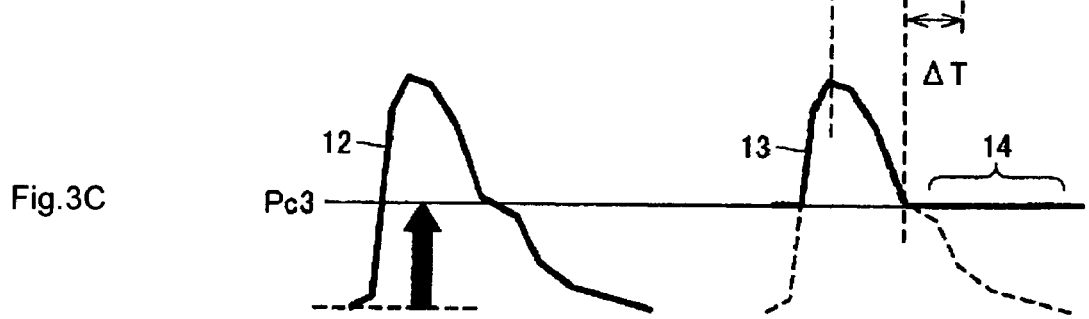

Next, as shown in FIG. 3B, when the cuff pressure is increased to reach a cuff pressure Pc2 higher than the systolic pressure, the arterial pressure becomes lower than the cuff pressure in one heartbeat period, and the arterial vessel is temporarily crushed by the cuff pressure in a certain period (hereinafter, referred to as closure period) 14. Within the closure period 14, since the arterial volume is always zero, the waveform of the detected pulse wave signal is also flat. When the cuff pressure is further increased to reach a cuff pressure Pc3, as shown in FIG. 3C, the closure period 14 starts earlier. For example, when a time point at which the peak of amplitude of pulse wave in one heartbeat period is detected is set to a start point, the closure period 14 in FIG. 3B starts at a time T1, while at the higher cuff pressure Pc3 in FIG. 3C, it starts at a time T2, and the closure period 14 starts by time difference ΔT as shown in the figure.

Start timing of closure period 14 (hereinafter, referred to as closure start point) is a moment when the cuff pressure is equalized with the arterial pressure. Therefore, if the changes of cuff pressure and arterial pressure at closure start points of two closure periods 14 can be detected, the arterial pressure at other moment than the closure start point can be estimated. Specifically, the systolic pressure and diastolic pressure, and also mean blood pressure can be calculated.

As shown in FIG. 3A, waveforms of pulse waves (arterial volume waveforms 13) detected at a cuff pressure under the systolic pressure being regarded to be similar to arterial pressure changes relatively indicate the level of the arterial pressure at the moment in one heartbeat period. In particular, they suggest the relative relation of the systolic pressure, diastolic pressure and mean pressure most important clinically and the arterial pressures at other moments. The waveforms of the pulse waves can be matched in time with those of other pulse waves by the peak point of the amplitude.

On the basis of these facts, in the embodiment, the scale of similar waveforms (pulse wave waveforms) changing similarly to the arterial pressure changes in one heartbeat period is determined, and the determined scale of similar waveforms is matched with the scale of the waveforms showing arterial pressure changes, thereby calculating the blood pressure. That is, by detecting the closure start points of two closure periods 14 and momentary arterial pressures at each closure start point, the arterial pressure at other points is estimated geometrically by the detected information and similar waveforms.

Stored Data in Memory

Figure 4:
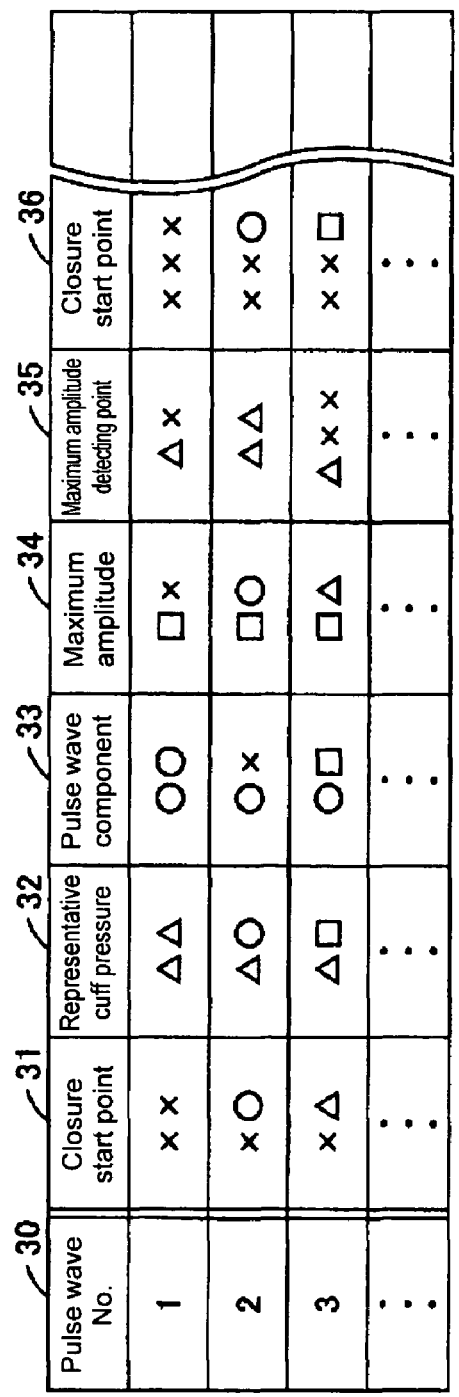
FIG. 4 is a diagram showing an example of contents stored in a memory.

The memory 64 stores, in every pulse wave detected during measurement for measuring the blood pressure as shown in FIG. 4, a pulse wave number 30 for specifying the pulse wave, pulse wave start point data 31 mentioned below, representative cuff pressure data 32 mentioned below, pulse wave component data 33, maximum amplitude data 34, maximum amplitude detection moment data 35, and closure start point data 36. The pulse wave component data 33 is shown by matching the time information in one heartbeat period with the level of waveform of pulse wave changing in one heartbeat period.

Operation of Blood Pressure Measuring Apparatus

Assume herein that the blood pressure measuring function by the first measuring unit 21 is selectively activated by manipulation of the mode switch 10C.

(Overall Operation)

Figure 5:
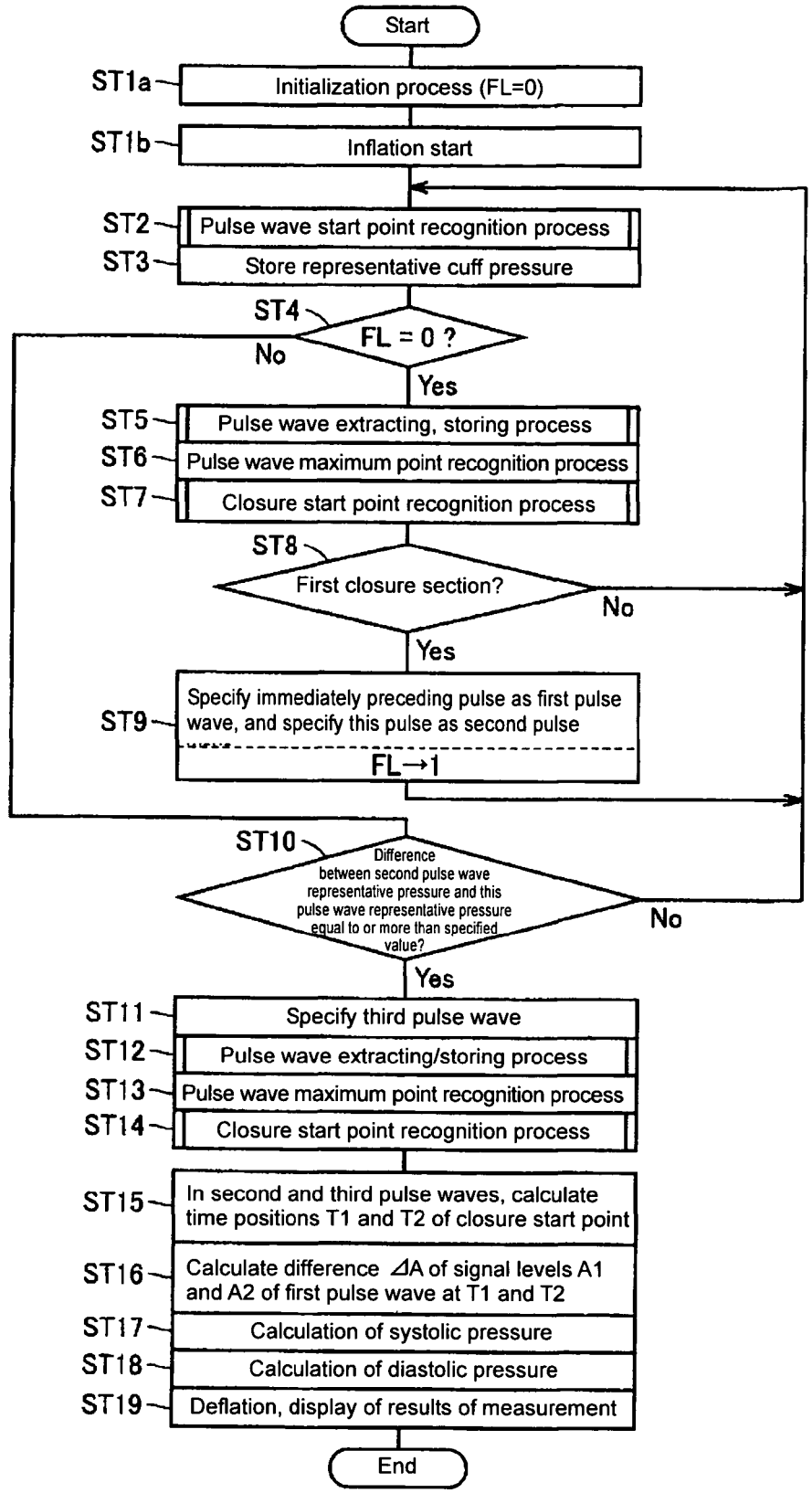
FIG. 5 is a flowchart showing an overall operation of blood pressure measurement.

Referring to the flowchart in FIG. 5, description will be give of an overall operation for blood pressure measurement by the first measuring unit 21 of the blood pressure measuring apparatus. The program according to the flowchart is preliminarily stored in the memory 64 of the MPU 6, and is executed by the control of the MPU 6.

The cuff 1 is wound around the arm of a person to be measured, and left and right electrodes VL and VR and ground electrode GD for simultaneous electrocardiographic measurement parallel to blood pressure measurement by the MPU 6 are also attached to parts of the body of the person. When the user turns on the power switch 10A, a initialization process is executed (step (ST) 1*a*). In the initialization process, an initial value (=0) is set to a flag FL.

Later, when the user turns on the start switch 10B, blood pressure measurement and electrocardiographic measurement are executed simultaneously. Detail of process for electrocardiographic measurement will not be described herein.

When blood pressure measurement starts, the MPU 6 starts to drive a pump (not shown) of the inflating unit 2; therefore, the cuff 1 is inflated, and the cuff pressure begins to increase (ST 1*b*). As the cuff pressure increases, the cuff pressure signal is supplied to the MPU 6 by way of the cuff pressure detector 4 and amplifier/AD converter 5.

The start point of pulse wave of every one heartbeat period, that is, every beat is recognized on the cuff pressure signal by executing the pulse wave start point recognition process (ST 2). While detecting the pulse wave start point, the pulse wave is specified, and the specified pulse wave is stored in the memory 64 as the pulse wave number 30, and the corresponding pulse wave start point data 31 is also stored. Detail of pulse wave start point detection will be described later. The cuff pressure (hereinafter, referred to as representative cuff pressure) corresponding to each pulse wave stored in the memory 64 in every beat is detected by the cuff pressure detector 4, and stored as data 32 in the memory 64 in correspondence (ST 3). The representative cuff pressure may be a cuff pressure at any moment in one heartbeat period, but in this embodiment the representative cuff pressure is the value of the cuff pressure signal detected at start point of pulse wave.

Figure 6:
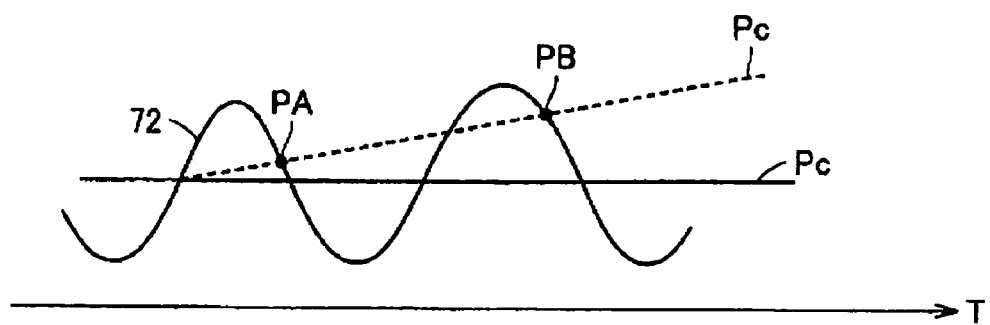
FIG. 6 is a diagram showing another detecting method of representative cuff pressure.

Herein, the representative cuff pressure is the cuff pressure corresponding to the start point of pulse wave, but actually, as shown in FIG. 6, the cuff pressure Pc changes as indicated by broken line, not by solid line, in relation to the pulse wave 72, and a high precision of measurement is achieved by setting the cuff pressure PA (PB) at the closure start point as the representative cuff pressure.

Consequently, it is determined whether the flag FL for controlling the processing action is zero or not (ST 4). If determined to be zero, on the basis of the recognized pulse wave start point, the MPU 6 extracts the pulse wave component from on the cuff pressure signal in this heartbeat period, and stores in the memory 64 as data 33 (ST 5). Next, the level of maximum amplitude of the waveform of the pulse wave and the moment of maximum level are recognized, and stored in the memory 64 as data 34 and 35 (ST 6).

In the next process, concerning the pulse wave in one heartbeat unit stored in the memory 64, closure start point recognition process is executed for recognizing the closure start point, and the recognized closure start point is stored in the memory 64 as data 36 (ST 7). Detail of this closure start point recognition process will be described later. However, if the cuff pressure is equal to or less than the diastolic pressure, there is no closure period in the pulse waves to be processed. In this case, only the result of determining no closure period is stored in the memory 64 as data 36.

As the cuff pressure elevates, soon exceeding the systolic pressure, the MPU 6 determines that the pulse period having closure period is detected for the first time (ST 8). The pulse wave corresponding to the immediately preceding heartbeat (that is, the finally detected pulse wave out of the pulse waves not having closure period) is specified as first pulse wave, and the pulse wave of this heartbeat (that is, the first detected pulse wave out of the pulse waves having closure period) is specified as second pulse wave, and the flag FL is updated to 1 in order to show that the first and second pulse waves are specified (ST 9). The first pulse wave is not limited to the pulse wave of the immediately preceding heartbeat, but the pulse wave of the immediately preceding heartbeat is larger in amplitude and smaller in noise as compared with the pulse wave of other preceding heartbeat, and therefore by using the pulse wave of the immediately preceding heartbeat, a high precision of measurement can be obtained.

Then, back to ST 2 in order to repeat the same process for subsequent heartbeats, at process ST 3, the representative cuff pressure is detected as for the pulse wave of next heartbeat, and stored in the memory 64 as data 32, and the process advances to ST 4. At this time, the flag FL shows 1, and as a result of determination at process ST 4, the operation advances to next process (ST10).

The next process is to determine the difference of the representative cuff pressure stored in the memory 64 in correspondence to the second pulse wave (representative cuff pressure Pc2) and the representative cuff pressure stored in correspondence to the pulse wave detected at this moment, and determine if it is more than a specified value (for example, 10 mmHg) or not (ST 10). Successively, the cuff pressure continues to elevate gradually even in the period in which the difference is not more than the specified value (No in ST 10), and the pulse wave start point recognition process (ST 2) and representative cuff pressure storing process (ST 3) are executed repeatedly.

After that, when the increment of the representative cuff pressure about the pulse wave presently detected corresponding to the representative cuff pressure Pc2 exceeds a specified value (Yes in ST 10), the process goes to next step (ST 11). In this way, the process is advanced to next step after allowing a certain time to elevate by a specified cuff pressure (for example, 10 mmHg) after detection of the second pulse wave, which is because it is intended to maintain the precision in estimation of blood pressure by geometrical method as described later.

In the next process, the present heartbeat is specified as third pulse wave (ST 11), and the third pulse wave is processed according to steps ST 12 to ST 14. These processes are exactly same as those at steps ST 5 to ST 7, and the detailed description will not be given.

In this manner, the pulse waves (first pulse waves) not having closure period are captured (detected and stored) for one heartbeat, and the pulse waves (second and third pulse waves) having closure period are captured (detected and stored) for two heartbeats, and then the blood pressure is calculated as follows on the basis of the contents stored in the memory 64.

First, concerning the second and third pulse waves, time positions T1 and t2 of closure start point starting from the moment of maximum level of pulse wave amplitude (pulse wave waveform) are calculated on the basis of the contents stored in the memory 64 (ST 15).

Figure 7:
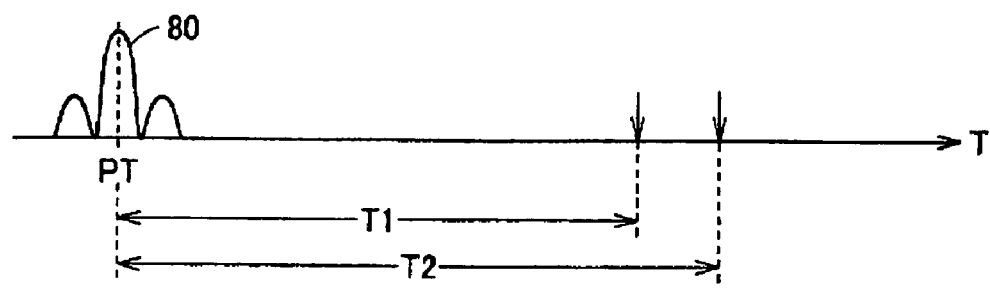
FIG. 7 is a diagram showing another detecting method of a time position of a closure start point.

The detecting method of time positions T1 and T2 is not limited to this method alone, and as shown in FIG. 7, for example, the moment PT of the maximum amplitude detected in every heartbeat about the electrocardiographic signals 80 (R waves) entered from the electrocardiographic detector 7 by the electrocardiographic measuring unit 63 is stored in the memory 64, and starting from this point, the time positions T1 and T2 of closure start point may be calculated.

Figure 8:
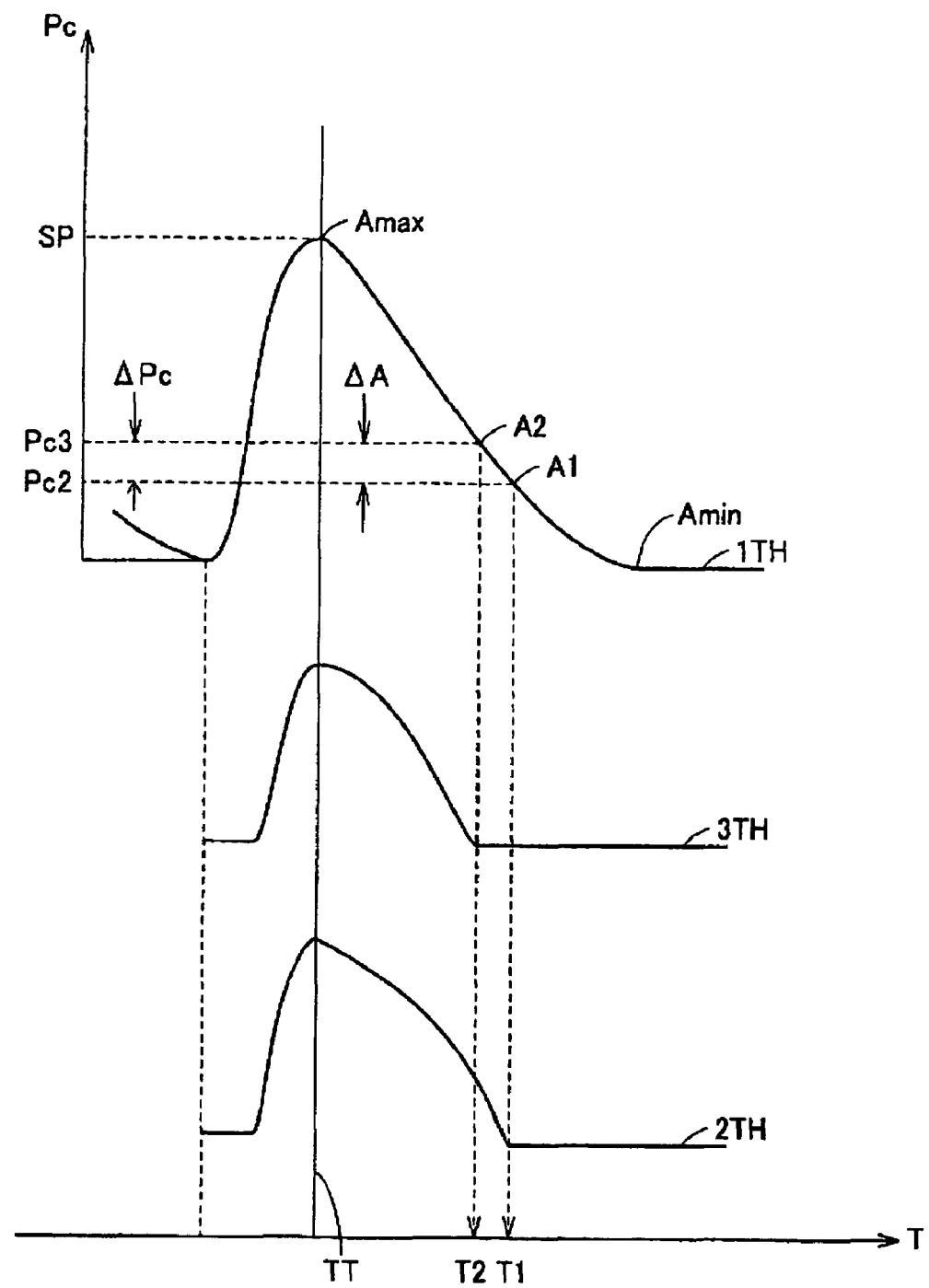
FIG. 8 is a descriptive diagram of calculating procedure of blood pressure on the basis of geometrical information.

Then, using the data of first, second and third pulse waves 1TH, 2TH and 3TH stored in the memory 64, the blood pressure is calculated on the basis of the geometrical information as shown in FIG. 8. By storing the data of first, second and third pulse waves 1TH, 2TH and 3TH in the memory 64, the scale of the pulse wave waveform is determined by using the stored data. By matching the determined scale of the pulse wave waveform with the scale of the waveforms showing pressure changes in the blood vessels, the blood pressures of systolic pressure and diastolic pressure are calculated.

First, the systolic pressure SP is calculated (ST 16, ST 17). Specifically, in FIG. 8, the first, second and third pulse wave waveforms are matched in time phase. That is, on the basis of the data 33, 34 and 35, the moments of the amplitudes of the second and third pulse waves 2TH and 3TH reaching the maximum level are matched in time phase on the basis of the axis TT of the moment of the amplitude of the first pulse wave 1TH reaching the maximum level. Corresponding levels (pressure levels) A1 and A2 are specified at the points on the time positions T1 and T2 of closure start point corresponding to the waveform of the first pulse wave 1TH. As a result, the change amount $\Delta A$ (A2=A1) of the pulse wave waveform (first pulse wave 1TH) corresponding to the lapse of time from time position T2 to T1 is specified, and the scale of the pulse wave waveform is determined.

Cuff pressure change amount $\Delta Pc$ (=Pc3−Pc2) is determined about he first pulse wave 1TH corresponding to the specified change amount (=$\Delta A$) from level A1 to A2. The ratio of $\Delta A$ and $\Delta Pc$ is the similarity ratio of waveform of arterial pressure change and waveform of pulse wave. Change amount of first pulse wave 1TH (=A max−A2) is determined between level A2 and amplitude maximum value A max detected at process ST 6 of first pulse wave 1TH. By adding the product of the ratio of the change amount (=A max−A2) divided by the change amount ΔA (=A2−A1) and the cuff pressure change amount ΔPc to the cuff pressure Pc3, the systolic pressure SP can be determined. The procedure of this series of operations is shown in formula (1):

$$SP=Pc3+(Pc3-Pc2)\times(A\max-A2)/\Delta A \quad (1)$$

wherein variables Pc2 and Pc3 show values of the representative cuff pressure of the data 32 stored in the memory 64, corresponding to the second and third pulse waves. In this case, the third pulse wave is supposed to be captured at a higher cuff pressure than the second pulse wave, and hence it is assumed Pc3>Pc2. Formula (1) may be also expressed as SP=Pc2+(Pc3−Pc2)×(A max−A1)/ΔA. Then, the diastolic pressure DP is calculated similarly in formula (2) (ST 18):

$$DP=Pc2-(Pc3-Pc2)\times(A1-A\min)/\Delta A \quad (2)$$

wherein variable Pc1 is the value of representative cuff pressure indicated by the data 32 stored in the memory 64 corresponding to the first pulse wave 1TH. Variable A min shows the minimum level of waveform of first pulse wave 1TH, which can be obtained easily as the waveform level of pulse wave corresponding to the pulse wave start point indicated by the data 31 in the pulse wave component indicated by the data 33. Formula (2) may be also expressed as DP=Pc3−(Pc3−Pc2)×(A2−A min)/ΔA.

Formula (1) and formula (2) show that the blood pressure can be calculated by using the similarity ratio on the basis of the geometrical information about the pulse wave waveforms.

After calculation of both systolic pressure SP and diastolic pressure DP, the air in the cuff 1 is exhausted by the quick deflating unit 3, and the cuff pressure is discharged, and the blood pressure calculation results are displayed in the display unit 9A through the output unit 9. This is the end of the operation (ST 19).

In this embodiment, the representative cuff pressure about the pulse wave of each heartbeat is expressed as the cuff pressure signal value at pulse wave start point, but it is not limited thereto. Strictly speaking, there is a time difference between the pulse wave start point and the closure start point used in blood pressure calculation process, and the cuff pressure continues to increase in this period. Therefore, when the representative cuff pressures of the second and third pulse waves are expressed by the cuff pressures detected at the closure start point, the precision of blood pressure calculation will be much enhanced.

Parallel to calculation of blood pressure, the pulse pressure (difference of systolic pressure and diastolic pressure) may be also calculated. The pulse pressure can be calculated on the basis of the difference of the maximum level A max and minimum level A min and the similarity ratio.

The following is the description about pulse wave start point recognition process (ST 2), pulse wave extracting process (ST 5, ST 12), and closure start point recognition process (ST 7, ST 14) shown in the flowchart in FIG. 5.

(Pulse Wave Start Point Recognition Process)

Figure 9:
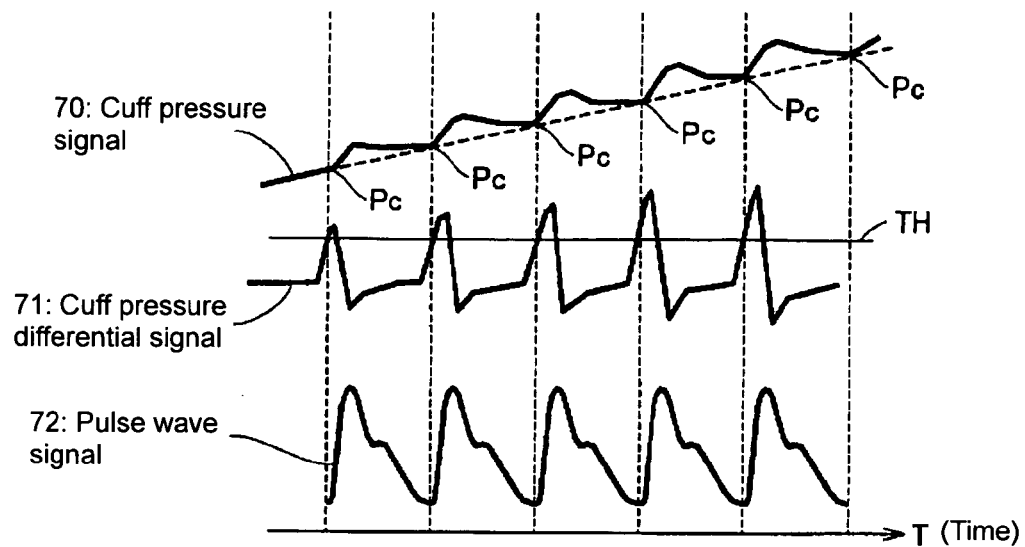
FIG. 9 is a descriptive diagram of procedure of pulse wave start point recognition.

Concept of pulse wave start point recognition is shown in FIG. 9. FIG. 9 shows a cuff pressure signal 70 in the process of time T, a cuff pressure differential signal 71 obtained by differentiating the cuff pressure signal 70, and a pulse wave signal 72 showing the pulse wave extracted from the cuff pressure signal 70. The cuff pressure signal 70 is a signal extracted by the cuff pressure detector 4, and a pulse wave is superposed. Relating to the cuff pressure signal 70, a cuff pressure Pc is shown, which is a pressure applied by the MPU 6 to the cuff 1 by way of the inflating unit 2. The pulse wave start point can be recognized in various methods, and generally about the cuff pressure signal 70, by emphasizing the rising point of the pulse wave by high pass filter processing or differentiating process by the MPU 6, it is recognized as the moment of the amplitude of such enhanced filter output signal or differential signal (cuff pressure differential signal 71) beginning to surpass the specified threshold. This is based on the knowledge that the pulse wave is most steep in one heartbeat period at the initial rising moment toward the peak of amplitude.

(Pulse Wave Extraction Process)

The pulse wave signal 72 is extracted from the cuff pressure signal 70 in various methods. In this embodiment, for example, by removing the basic variation point of cuff pressure Pc, that is, gradual increment portion from the original cuff pressure signal 70, the pulse wave component (pulse wave signal 72) is extracted.

As shown in FIG. 9, a pulse wave component is superposed on the cuff pressure signal 70 as indicated by solid line in the portion indicated by broken line of gradual increase of cuff pressure Pc. The cuff pressure gradual increment portion indicated by broken line is the pulse wave start point linking the adjacent pulse wave start points by straight line after recognized in each heartbeat. The cuff pressure gradual increment component of broken line is subtracted from the original cuff pressure signal 70, and the pulse wave component is obtained. The pulse wave signal 72 is a magnified result of such extracted pulse wave component.

(Closure Start Point Recognition Process)

As mentioned above, the closure period if the period of complete compression of the arteries by the operation of the cuff pressure. In this period, therefore, there is no arterial volume change, and the pulse wave waveform is almost flat. On the other hand, before the closure period, the amplitude level of pulse wave continues to decrease gradually from the maximum point of amplitude of pulse wave (this is decrease period). The closure start point at the boundary of the decrease period and closure period can be recognized in various methods, and herein it is based on detection of flex point of pulse wave waveform characteristically observed at the closure start point.

Figure 10:
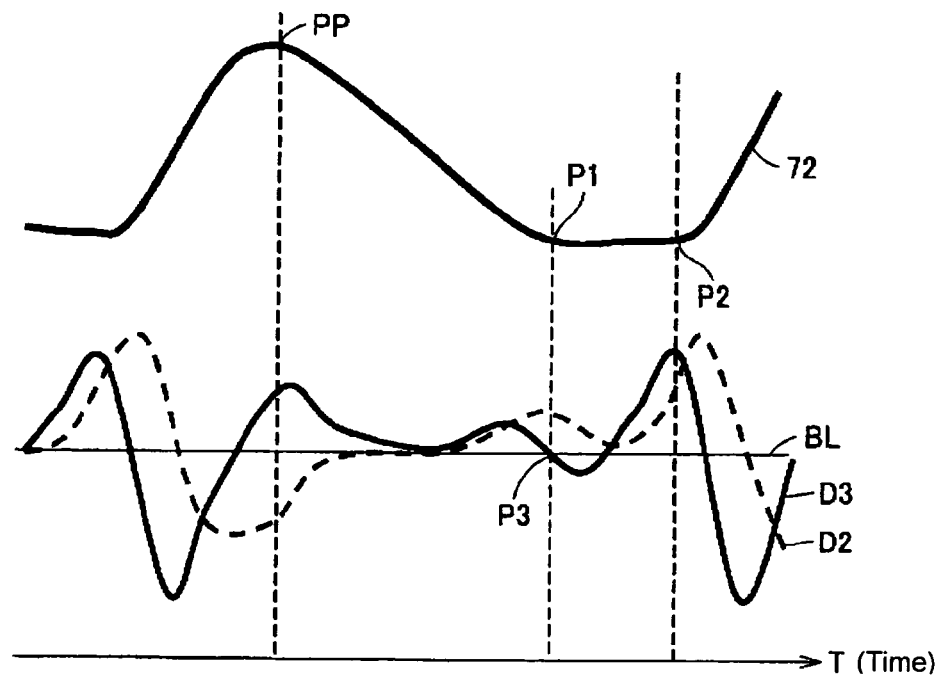
FIG. 10 is a descriptive diagram of procedure of closure start point recognition.

FIG. 10 shows a concept of recognition process of closure start point on the basis of differential waveform by differentiating the waveform of pulse wave. FIG. 10 shows the waveform of pulse wave signal 72 extracted by pulse wave extraction process, and waveforms of secondary differential signal D2 and tertiary differential signal D3 of pulse wave signal 72 in the process of time T. FIG. 10 also shows the base line BL for indicating level zero of secondary differential signal D2 and tertiary differential signal D3.

First, the MPU 6 calculates the waveforms of secondary and tertiary differential signals D2 and D3 about the extracted pulse wave signal 72. Starting from the amplitude peak point PP (amplitude maximum point) of the pulse wave signal 72, the point of transfer of waveform of secondary differential signal D2 from negative to positive in the elapse direction of time T is detected. At peak point PP, the waveform of the pulse signal 72 is a convex waveform, and the waveform of the secondary differential signal D2 is a negative value, but when the time T passes from the peak point PP to come to the amplitude level decline section of pulse wave signal 72, the waveform of the secondary differential signal D2 changes from negative to zero and to positive. At the closure start point, the waveform of the secondary differential signal D2 reaches the maximal point. Since various artifacts are mixed in the waveform of the pulse wave signal 72, the closure start point may be falsely recognized if only the peak (maximal point) of the waveform of the secondary differential signal D2 is determined. Accordingly, when the MPU 6 recognizes that the waveform of the tertiary differential signal D3 is changed from positive to negative at the time of the waveform of the secondary differential signal D2 reaching the maximal point (that is, when the intersection P3 of the base line BL and waveform of third differential signal D3 is detected), this intersection is finally recognized to be the closure start point P1. Detecting the closure start point P1, after lapse of closure period, the pulse wave start point P2 of next pulse is detected.

Figure 11:
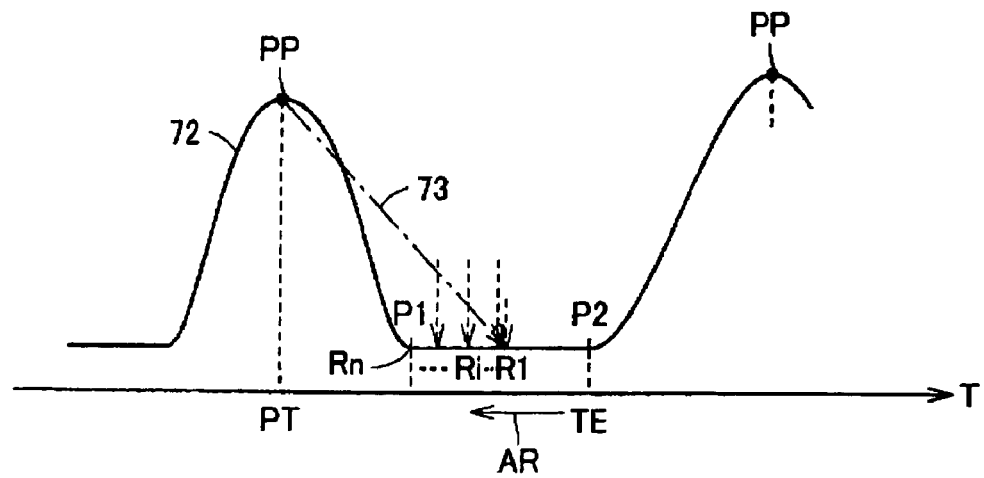
FIG. 11 is a descriptive diagram of another procedure of closure start point recognition.
Figure 12:
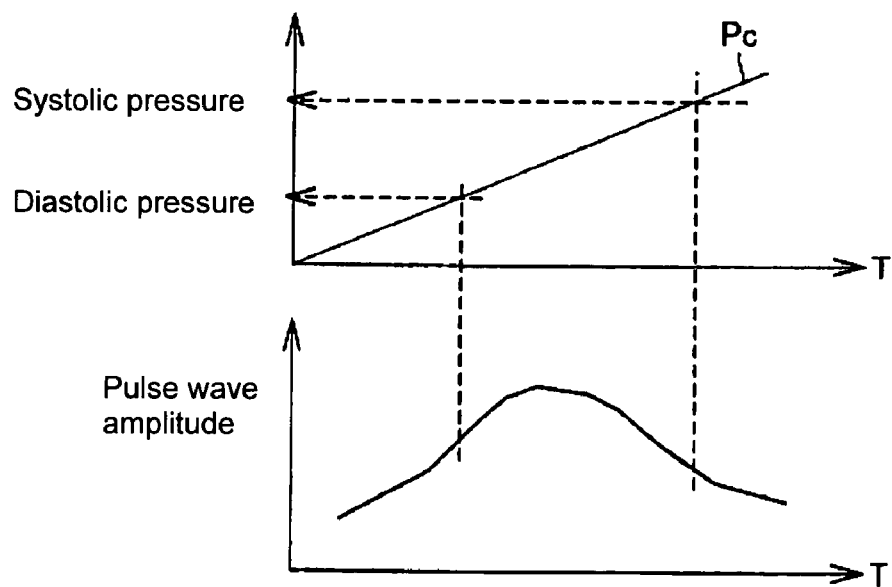
FIG. 12 is a diagram showing a concept of a blood pressure estimating method according to a conventional oscillometric method.

The closure start point may be also detected as shown in FIG. 11. FIG. 11 shows the pulse wave signal 72 in the process of time T, and slope signal 73 showing the slope of the pulse wave signal 72. Following up the time T in the direction (arrow AR direction) to the point PT corresponding to the maximum amplitude PP of the heartbeat period from the terminal end point TE of the heartbeat period defined by the rise point (pulse wave start point P2) toward the maximum amplitude PP of the pulse wave signal 72 of the next heartbeat period, among candidate points Ri (i=1, 2, 3, ..., n) of plural closure start points, the closure start point P1 may determined at the candidate point Ri showing the maximum difference between the level (about 0) of slope signal 73 before the candidate point R1 at the intersection of the pulse wave signal 72 and slope signal 73 and the level of the slope signal 73 corresponding to the candidate point Ri after this candidate point R1. In FIG. 11, the candidate point Rn is determined as the closure start point P1.

The embodiment disclosed herein shows only examples and is not intended to limit whatsoever. The scope of the invention is shown by the claims not by the explanation above, and all changes that fall within metes and bounds of the claims, and equivalence of such metes and bounds thereof are therefore intended to be embraced by the claims.

According to the invention, the blood pressure can be detected by using the scale of similar waveforms changing similarly to pressure changes in blood vessels detected in one heartbeat period; therefore, the blood pressure can be measured in a short time. That is, according to one aspect of the invention, once determining the scale of similar waveforms, the similarity ratio of matching the determined scale of similar waveforms with the scale of waveforms showing changes of pressure in the blood vessels can be easily obtained by the ratio of the difference of levels at two moments and the difference of oppressing pressure values detected by the oppressing pressure detecting means corresponding to the two moments. The levels at the two moments are somewhere between the maximum level and minimum level, and hence it is possible to measure without oppressing to the maximum level, that is, the maximum blood pressure. Since it is possible to measure by detecting only the levels of the two moments and the oppressing pressure value, the measuring time can be shortened.

According to another aspect of the invention, by detecting the first, second and third pulse waves by the pulse wave detecting means and storing the waveform levels of the first, second and third pulse waves in the storing means for one heartbeat period, the scale of similar waveforms is determined on the basis of the similarity ratio by the processing means, and the blood pressure can be measured by matching the detected scale of similar waveforms with the scale of the waveforms showing pressure changes in the blood vessels.

What is claimed is:

1. A blood pressure measuring apparatus comprising:
   oppressing means for oppressing blood vessels of a human body;
   oppressing pressure detecting means for detecting the oppressing pressure value on the blood vessels by the oppressing means;
   similar waveform detecting means for detecting similar waveforms changing similarly to pressure changes in the blood vessels oppressed by the oppressing means in one heartbeat period; and
   blood pressure calculating means for determining the scale of the similar waveforms detected by the similar waveform detecting means, and calculating the blood pressure by matching the determined scale of similar waveforms with the scale of waveforms showing pressure changes in the blood vessels, wherein
   the blood pressure calculating means includes:
   level detecting means for detecting the level of the similar waveforms in one heartbeat period; and
   means for determining the scale of the similar waveforms on the basis of the similarity ratio indicated by the ratio of the difference of levels at two moments of maximum level and minimum level detected by the level detecting means and the difference of the oppressing pressure values detected by the oppressing pressure detecting means corresponding to the two moments, and matching the determined scale of similar waveforms with the scale of the waveforms showing pressure changes in the blood vessels.

2. The blood pressure measuring apparatus according to claim 1, wherein
   the two moments correspond to the starting moments of closure of the blood vessels by the two different oppressing pressure values to the blood vessels by the oppressing means.

3. The blood pressure measuring apparatus according to claim 1, wherein
   the similar waveforms are waveforms of pulse waves derived from pulsation components of volume changes of the blood vessels caused by oppression by the oppressing means.

4. The blood pressure measuring apparatus according to claim 1, wherein
   the blood pressure calculating means includes systolic pressure calculating means for calculating the oppressing pressure value corresponding to the maximum level as the systolic pressure, on the basis of the difference between the maximum level detected by the level detecting means and one level of the levels at two moments detected by the level detecting means, the oppressing pressure value detected by the oppressing pressure detecting means corresponding to the moment of the one level, and the similarity ratio.

5. The blood pressure measuring apparatus according to claim 1, wherein
   the blood pressure calculating means includes diastolic pressure calculating means for calculating the oppressing pressure value corresponding to the minimum level as the diastolic pressure, on the basis of the difference between the minimum level detected by the level detecting means and one level of the levels at two moments detected by the level detecting means, the oppressing pressure value detected by the oppressing pressure detecting means corresponding to the moment of the one level, and the similarity ratio.

6. A blood pressure measuring apparatus comprising:
oppressing means for oppressing blood vessels of a human body;
similar waveform detecting means for detecting similar waveforms changing similarly to pressure changes in the blood vessels oppressed by the oppressing means in one heartbeat period; and
blood pressure calculating means for determining the scale of the similar waveforms detected by the similar waveform detecting means, and calculating the blood pressure by matching the determined scale of similar waveforms with the scale of waveforms showing pressure changes in the blood vessels, wherein
the similar waveform detecting means includes pulse wave detecting means for detecting the waveform of pulse waves derived from pulsation components of volume changes of the blood pressure caused by oppression by the oppressing means as the similar waveforms, and
the blood pressure calculating means includes:
storing means for storing, in the one heartbeat period, the levels of waveforms of first, second and third pulse waves detected by the pulse wave detecting means by first oppressing pressure not closing the blood vessels by the oppressing means, and second oppressing pressure and third oppressing pressure for closing the blood vessels;
level specifying means for specifying the second and third level corresponding to the starting moments of closure of the waveforms of the second and third pulse waves, of the waveform of the first pulse wave matched in time phase with the waveforms of the second and third pulse waves, in the contents stored in the storing means; and
processing means for determining the scale of the similar waveforms on the basis of the difference of the second level and third level specified by the level specifying means, and the similarity ratio indicated by the ratio of the difference of the second oppressing pressure and third oppressing pressure, and matching the determined scale of the similar waves with the scale of the waveform indicating the pressure changes in the blood vessels.

7. The blood pressure measuring apparatus according to claim 6, wherein
the processing means divides a second change amount as change amount of waveform of the first pulse corresponding to the difference between the maximum level of the waveform of the first pulse stored in the storing means and the second level, by a first change amount as change amount of waveform of the first pulse wave corresponding to the difference of the second level and third level, multiplies the obtained amount by the difference of the second oppressing pressure and third oppressing pressure, adds the second oppressing pressure to the product, and calculates the result as the systolic pressure.

8. The blood pressure measuring apparatus according to claim 6, wherein
the processing means divides a second change amount as change amount of waveform of the first pulse corresponding to the difference between the minimum level of the waveform of the first pulse stored in the storing means and the third level, by a first change amount as change amount of waveform of the first pulse wave corresponding to the difference of the second level and third level, multiplies the obtained amount by the difference of the second oppressing pressure and third oppressing pressure, subtracts the product from the third oppressing pressure, and calculates the result as the diastolic pressure.

9. The blood pressure measuring apparatus according to claim 6, wherein
the waveforms of the first, second and third pulse waves are matched in time phase on the basis of the moment corresponding to the maximum levels of the waveforms stored in the storing means.

10. The blood pressure measuring apparatus according to claim 9, further comprising:
electrocardiographic detecting means for detecting electrocardiographic signals from a person to be measured simultaneously with measurement of blood pressures, wherein
the waveforms of the first, second and third pulse waves are matched in time phase on the basis of the characteristic waveforms in the electrocardiographic signals detected by the electrocardiographic detecting means in the one heartbeat period.

11. The blood pressure measuring apparatus according to claim 10, wherein
the characteristic waveforms show the peak of R waves.

12. The blood pressure measuring apparatus according to claim 1 or 6, wherein
the blood pressure calculating means includes pulse pressure calculating means for calculating the pulse pressure.

13. The blood pressure measuring apparatus according to claim 12, wherein
the pulse pressure calculating means calculates the pulse pressure on the basis of the difference of the maximum level and minimum level and the similarity ratio.

14. The blood pressure measuring apparatus according to claim 2 or 6, wherein
the blood pressure calculating means further includes closure start point detecting means for detecting the start moment of closure of the blood vessels, and
the closure start point detecting means detects the moment of start of closure by selecting the candidate moment showing the maximum difference between the slope level corresponding to the candidate moments of the similar waveforms and the slope level corresponding to the immediately preceding candidate moment, among a plurality of candidate moments from terminal end moment of the one heartbeat period to the moment corresponding to the maximum level.

15. The blood pressure measuring apparatus according to claim 1 or 6, further comprising:
a first measuring unit including the similar wave detecting means and blood pressure calculating means; and
a second measuring unit for measuring the blood pressure according to the oscillometric method while gradually changing the oppression to the blood vessels by the oppressing means, wherein
one of the first and second measuring units is selectively activated.

* * * * *